United States Patent [19]

Andersson et al.

[11] 4,015,935
[45] Apr. 5, 1977

[54] METHOD AND APPARATUS FOR FEEDING AND DISCHARGING A CONTINUOUSLY OPERATING AUTOCLAVE

[75] Inventors: Bror Lennarth Andersson; Nils Arne Fahlvik, both of Getinge, Sweden

[73] Assignee: Aktiebolaget Electrolux, Stockholm, Sweden

[22] Filed: Nov. 21, 1975

[21] Appl. No.: 634,252

[30] Foreign Application Priority Data

Dec. 2, 1974 Sweden .............................. 7415089

[52] U.S. Cl. .............................. 21/2; 21/80; 99; 104; 99/362; 366; 426/407; 521

[51] Int. Cl.² ...................... A23L 3/04; A61L 1/00; A61L 3/00

[58] Field of Search ................ 21/80, 103, 104, 56, 21/58, 99, 2; 426/407, 409, 521–523; 99/362, 366, 361, 368; 214/1 BB, 1.4, 17 B, 23; 198/106; 49/68; 302/62; 243/20–22, 26

[56] References Cited

UNITED STATES PATENTS

| 1,230,811 | 6/1917 | Shippee | 214/17 B |
| 1,346,158 | 7/1920 | Baily et al. | 214/17 B |
| 2,094,753 | 10/1937 | Ryan et al. | 214/17 B |
| 2,468,794 | 5/1949 | Wilbur | 214/17 B |
| 3,633,770 | 1/1972 | Howard | 214/17 B |
| 3,762,934 | 10/1973 | Reimert | 426/407 |
| 3,773,189 | 11/1973 | Kitamura et al. | 214/1 BB |

FOREIGN PATENTS OR APPLICATIONS

| 238,694 | 1/1960 | Australia | 21/80 |
| 1,962,428 | 6/1971 | Germany | 99/361 |
| 1,136,610 | 3/1966 | United Kingdom | 21/80 |

*Primary Examiner*—Barry S. Richman
*Assistant Examiner*—Bradley Garris
*Attorney, Agent, or Firm*—Alfred E. Miller

[57] ABSTRACT

A feed and discharge assembly for a continuous autoclave having an internal conveyor. The articles to be processed in the autoclave are placed in perforated tube-like containers and transported to a location adjacent to a feed lock in the autoclave and inserted through a valve to the internal conveyor of the autoclave. The articles, after processing, are removed from the autoclave through a valve and a discharge lock to the exterior of said autoclave.

7 Claims, 8 Drawing Figures

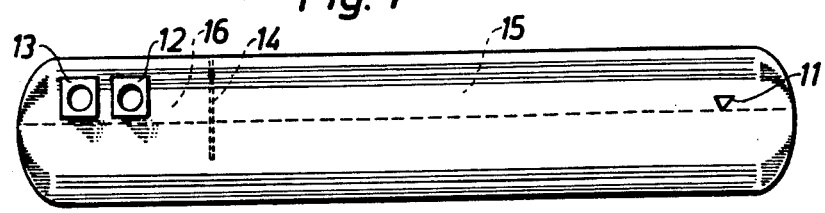
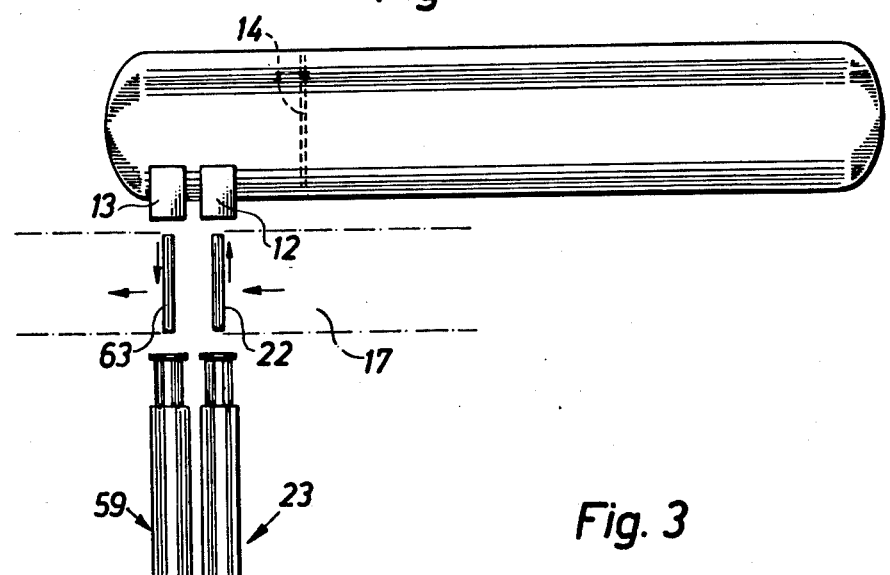
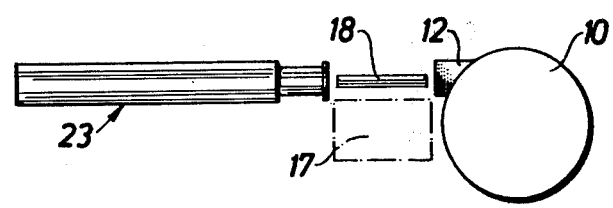
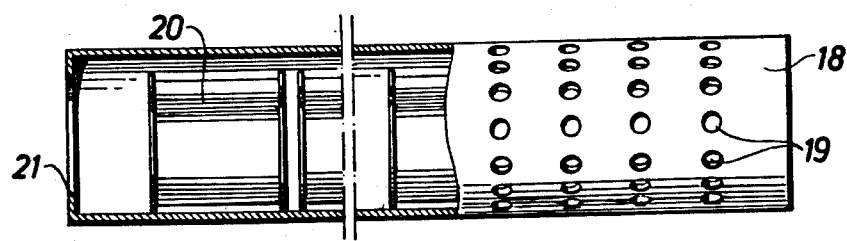

METHOD AND APPARATUS FOR FEEDING AND DISCHARGING A CONTINUOUSLY OPERATING AUTOCLAVE

BACKGROUND OF THE INVENTION

Continuously operating autoclaves are known, however the apparatus is spread out and occupies a great deal of space. This is particularly true with respect to hydrostatic cookers. Moreover, in autoclaves having some kind of openings for introducing and discharging articles to be processed, an amount of working medium is lost when the articles are introduced or removed from the autoclave thereby necessitating collecting vessels, and conduits with pumps to return the escaped working medium. In both types of known autoclaves, large heat losses occur.

SUMMARY OF THE INVENTION

It is an object of the present invention to provide a compact autoclave which has relatively small heat losses during operation. This object is fulfilled by means of an arrangement whereby perforated containers housing the articles to be treated in an aligned formation are passed through a lock in an autoclave wall to be transported by an internal conveyor within the autoclave. The containers, with the articles that have been processed, eventually are discharged from the autoclave through another lock. This autoclave arrangement is considerably more compact than previously known autoclave arrangements and the heat losses are substantially reduced.

In order that the invention will be more clearly understood, it will now be disclosed in greater detail with reference to the accompanying drawings, in which:

FIG. 1 is a side elevation view of a continuously operating, horizontally disposed autoclave constructed in accordance with the teachings of the present invention.

FIG. 2 is a top plan view of the autoclave shown in FIG. 1, and additionally showing the means for conveying articles to be processed through the autoclave.

FIG. 3 is an end view of the autoclave as seen from the right hand side.

FIG. 4 shows on a larger scale, partly in elevation and partly in section, a perforated tube-like container for conveying articles to be processed through the autoclave.

SUMMARY OF THE PREFERRED EMBODIMENT

Figure 5:
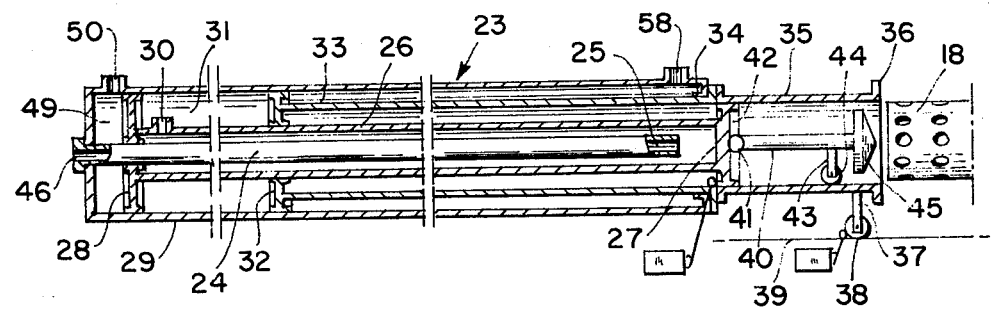
FIG. 5 is a sectional view, on an enlarged scale, of the feeding assembly for the tube-like containers carrying the articles to be inserted into the autoclave for processing.

Referring to FIGS. 1–3, the articles to be treated are introduced into an autoclave 10 that has a heated liquid bath, which can be water at a level 11. In the autoclave, the articles move on a continuous conveyor (not shown). The autoclave is furthermore charged and discharged with articles at one end by means of locks 12, 13 connected into the autoclave 10 above the liquid level 11. Superatmospheric pressure is maintained in the space above the liquid level in the autoclave. This space, however, is divided by a wall 14 extending downwardly from the top of the autoclave. In one part 15 is a certain total pressure which is maintained by vapor emanating from the hot liquid and compressed air, whereas in the other part 16, which is situated above a colder mass of liquid, a corresponding total pressure is maintained substantially by means of compressed air. Thus, the locks operate mainly with air and without any significant heat loss or loss of the processing medium present in the autoclave.

In FIG. 2, an outer conveyor 17 is shown on which tube-like containers 18 as seen in FIG. 4 are moved towards the feed lock 12. The containers have perforations 19, and contain articles in the form of aligned cans 20. The containers further have open ends, and at least one end has an inwardly directed flange 21.

The products are prepared or produced in known manner and are packed in containers. Food products are, for example, prepared and packed in cans 20. Infusion solutions or other pharmaceutical products are manufactured and filled into ampoules, for example constituted of plastic, which are then sealed. The cans are introduced in a row into each container 18 carried on the conveyor 17, which preferably operates stepwise and advances the tubes to a position 22 in front of the entrance to the lock 12. When this occurs, a feeding device 23 is started, which is shown in greater detail in a sectional view in FIGS. 5 and 6.

The feeding device comprises a system of cylinders and pistons therein of a length sufficient to enable the parts to perform movements beyond the length of the tubes 18, which in a suitable embodiment is 2.4 m. The feeding device 23 is provided with an inner pipe 24 whose front end 25 opens into and is surrounded by a second pipe 26, which has one closed end 27 while its other end is connected to a piston 28 sealing on the one hand the inner pipe 24 and on the other hand the outer pipe 29. Adjacent the piston 28, the second pipe 26 has an opening 30 communicating with a space 31, which is defined on the one hand by the outer pipe 29, and on the other hand by the piston 28 and a piston 32, thereby sealing the outer pipe 29 from the second pipe 26. Furthermore, the piston 32 is connected to a cylinder 33 and movable within a seal 34 at one end of the outer pipe 29. Thus, the cylinder 33 is capable of passing out of this pipe 29. Moreover, outside of the outer pipe 29, the cylinder 33 is lengthened by a sleeve 35, which at its front end has a seal 36 adapted to abut a surface, provided for the purpose, of the feed lock 12 and be sealed therewith.

The front end of the sleeve 35 has an exterior support leg 37 provided with a roller 38 on a guide rail 39. In the sleeve 35 is a piston rod 40 connected by an arm 41 to the second pipe 26 and to a piston 42 arranged in a sealing manner with the sleeve 35. The front end of the rod 40 has a support leg 43 with a roller 44, adapted to roll in the sleeve 35, and a head 45 by which a container 18 can be moved forward.

Figure 6:
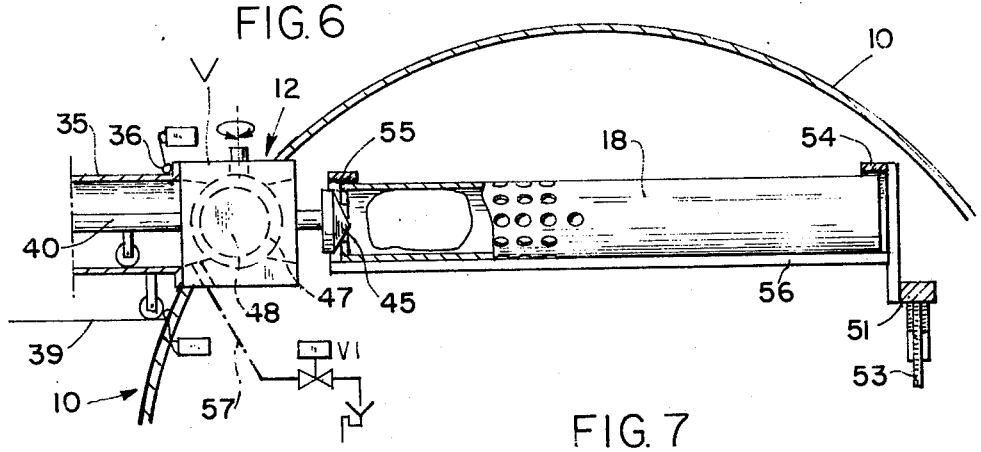
FIG. 6 is another sectional view of the feeding assembly showing the valve and its function.

In FIG. 5, the feeding system 23 is shown in the initial position with a container 18 placed ahead of the feed lock. FIG. 6 illustrates the position of the container after which the feeding step has just been performed. The mode of operation is as follows:

A pressure medium, for example compressed air, is admitted by a conduit into the left end 46 of the inner pipe 24 and the pressure medium is then introduced into the space 31 through opening 30. Thus, the piston 32 is acted upon so that the cylinder 33 and hence the sleeve 35 are moved forwards to enclose a container 18. The movement continues until the seal 36 of the sleeve abuts a surface of the lock 12 in a sealing manner. The latter comprises a ball valve V having a turnable tap 47 with a through hole 48. The valve is opened by turning the tap through 90° from a fully blocked position to a fully open position, and then compressed air from the interior of the autoclave 10 flows through the valve and into the space in the sleeve 35 so that the same pressure prevails in the autoclave as in the sleeve 35. A pressure medium is introduced into a space 49 in the left end of the feeding assembly by a connection 50 communicating with a pressure medium conduit (not shown). Thus, the piston 28 is acted upon in such a manner that the inner pipe 26 moves forwards, and the piston 42 and the piston rod 40 perform the same movement in the sleeve 35. The head 45 then abuts the perforated container 18, and moves it through the valve 12 into the autoclave, in which a continuous conveyor operates. The conveyor comprises two conveyor chains 51, of which only one is shown. The chains are driven by chain wheels 53, and have carriers 54, 55 consisting of rings connected by a spacing and guiding rail 56 for each container 18.

The movement of the container 18 onto the conveyor 51, 53–56 causes the piston rod 40 to move forwards so that the head 45 advances into the autoclave. At the same time the piston 42 has moved forwards a considerable distance in the sleeve 35. Thus, in the space in the sleeve 35 in front of the piston 42, at the right side of FIG. 5, there is only compressed air supplied from the autoclave chamber. When the container 18 has been fed in, the piston rod 40 is moved back through the valve V so that the latter can close. This movement of the piston rod is effected by introducing a pressure medium into the connection 46 of the inner pipe 24 so that the pressure will act in the space 31. The piston 32 is in its right-hand end position and thus the piston 28 will be caused to move to the left in FIG. 5 towards its left-hand end position, carrying with it the second pipe 26 together with the piston rod 40. When the head 45 of the piston rod has passed the valve 12 and the latter has closed, another valve $V_1$ is opened in a pressure-equalizing conduit 57 and the pressure in the sleeve 35 is released. Then the movement of the second pipe 26 and the piston rod 40 to their left-hand end position is accomplished. At the same time, by admitting pressure medium through a connection 58 at the right-hand end of the system, the piston 32 is acted upon so that the cylinder 33 with the sleeve 35 are caused to move to their left-hand end positions.

Figure 8:
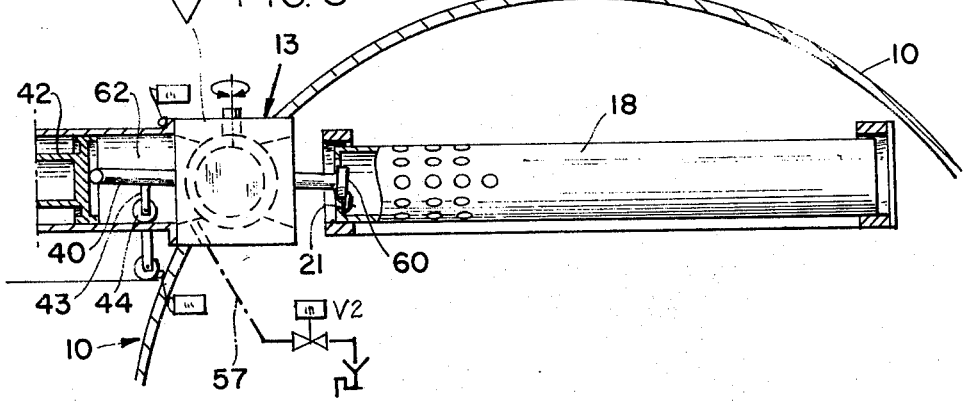
FIG. 8 is a sectional view similar to FIG. 6, however showing the discharge assembly of FIG. 7 in operation.

The conveyor 51, 53-56 in the autoclave operates in a stepwise fashion, and after a container 18 has been fed into the conveyor the latter advances one step at a time. When the treatment of the articles in the autoclave is completed the conveyor stops with the perforated container 18 in front of the discharge lock 13 (FIG. 8). Outside of the lock 13 a discharging device 59 operates in a manner corresponding to that of the feeding device 23. Therefore, only the details which are different from those already discussed will be described.

Instead of the feed head 45 the piston rod 40 has a device with a hook 60. The support leg 43 with roller 44 stands in the initial position on a cam guide 61 in the sleeve 35.

Figure 7:
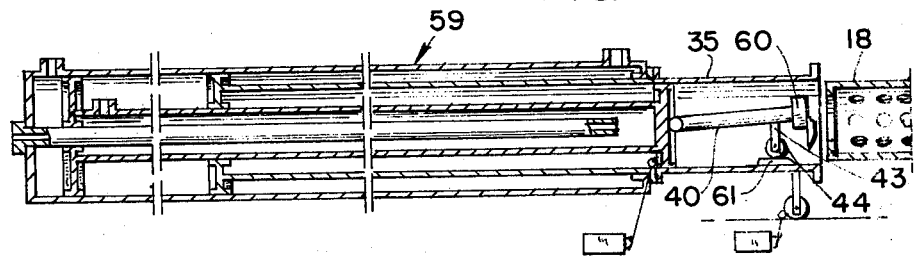
FIG. 7 is a sectional view, on an enlarged scale similar to FIG. 5 but showing the discharge assembly for said containers after the articles therein have been processed

For discharge of a container 18, the sleeve 35 is moved so as to abut the lock 13 in a sealing fashion. Then, the piston rod 40 is moved in a forward direction so far that the hook 60 is positioned adjacent to the valve, but outside of it. The valve is opened and compressed air from the autoclave flows through the valve into a space 62 in front of the piston 42. The piston rod 40 is then advanced so that the hook 60 passes through the valve and into the perforated container 18 through one end opening thereof, to thereby engage behind the flange 21. Then, the piston rod 40 is drawn back to its initial position and the container 18 is entrained out through the valve V, which then closes, A valve $V_2$ is opened in the pressure-equalizing conduit 57 so that the pressure in the space 62 is removed, after which also the cylinder with the sleeve 35 moves back to their initial position. At the end of the returning movement, the roller 44 of the support leg 43 of the rod 40 moves up on the cam guide 61 so that the engagement of the hook 60 with the container 18 is broken (FIG. 7). The container 18 in the position 63, as seen in FIG. 2, can now be brought by the conveyor 17 to a place where the sterilized articles may be removed and packed for transport, or moved to a storage area for sterile articles.

While the invention has been disclosed with reference to a limited number of embodiments, it will be understood that variations and modifications may be made therein. For example, the autoclave may be of other forms, such as disclosed in co-pending application Ser. No. 634,251 filed Nov. 21, 1975 (Case W-281, corresponding to Swedish application 7415088-9 filed in Sweden on Dec. 2, 1974), having a vertical partition dividing the bath into two parts, one at the feeding end and the other at the treatment end.

We claim:

1. In a feed and discharge arrangement for a continuously operating autoclave provided with a heated medium at super-atmospheric pressure and an internal conveyor for sterilization of articles carried by perforated containers; the improvement comprising: a feed lock for inserting said perforated containers into said autoclave and onto said internal conveyor, a discharge lock for withdrawing said perforated containers having treated articles therein from said autoclave, each of said locks being provided with a valve which in its open position has an aperture that is larger than the diameter of each of said perforated containers, each of said locks including at least two interfitting telescoping cylinders one of which is adapted to contain a perforated container and is provided with a front end creating a front sealing surface when abutting a part of said lock whereby the forward part of said one cylinder forms a locking chamber, a first means in the locking chamber of said feed lock for pushing said container therein through said valve and onto said internal conveyor, and a second means in the locking chamber of said discharge lock for discharging said container from said internal conveyor through said discharge lock valve and into the locking chamber of said discharge lock after said container has been transported to a position adjacent to said discharge lock.

2. The combination as claimed in claim 1 wherein at least one of the valves is disposed between the ambient and the interior space of said autoclave in which super-atmospheric pressure prevails.

3. The combination as claimed in claim 1 wherein each of said valves comprises a ball valve having a turnable tap and a through aperture which when the valve is in the open position said perforated container can pass therethrough.

4. The combination as claimed in claim 3 further comprising an external conveyor positioned outside and adjacent to said autoclave, said external conveyor being constructed and arranged to transport perforated containers charged with articles therein to a place aligned with the passage of said feed lock.

5. The combination as claimed in claim 1 wherein said second means comprises an inner piston rod operatively connected to at least one of said cylinders, said piston rod having a hook device at its free end for retracting said container through said discharge lock.

6. The combination as claimed in claim 5 wherein a downwardly extending support leg with a roller is mounted on said piston rod and adjacent to said hook device, said roller being adapted to ride on an inner surface of said locking chamber, and a cam lifting surface on said inner surface whereby when said roller rides on said cam surface the hook device is respectively lowered into and lifted out of engagement with the respective perforated container withdrawn from said autoclave.

7. A method for respectively feeding and discharging articles into an autoclave and onto an internal continuous conveyor in a heated liquid bath at superatmospheric pressure for sterilization comprising:
   a. placing articles to be processed in perforated containers,
   b. arranging said containers in aligned rows at a feed station leading into said autoclave,
   c. passing said containers through a feed lock at a feed station and into said autoclave and onto said continuous conveyor, and wherein said feed lock comprises a plurality of telescoping interfitting cylinders in which a forward part of one cylinder forms a locking chamber, and a valve, and a piston in said locking chamber, the method of passing said containers through a feed lock including the steps of:
      1. advancing the one cylinder to seal with the valve thereby forming said locking chamber and enclosing a perforated container within said locking chamber,
      2. opening the valve,
      3. advancing the piston so that the perforated container is moved through the feed lock and onto the conveyor in the autoclave,
      4. retracting the piston to a return position,
      5. closing the valve,
      6. equalizing the pressure between the locking chamber and the ambient by means of a conduit having a valve therein and connected to the feed lock, and
      7. returning the one cylinder to its initial position,
   d. treating said articles in said liquid bath, and
   e. discharging said treated articles through a discharge lock at a discharge station.

* * * * *